US00PP28715P2

(12) United States Plant Patent
Horvath

(10) Patent No.: US PP28,715 P2
(45) Date of Patent: Nov. 28, 2017

(54) ***PENNISETUM ALOPECUROIDES* PLANT NAMED 'RED ROCKET'**

(50) Latin Name: *Pennisetum alopecuroides*
Varietal Denomination: Red Rocket

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 93 days.

(21) Appl. No.: 14/545,844

(22) Filed: Jun. 29, 2015

(51) Int. Cl.
*A01H 5/02* (2006.01)

(52) U.S. Cl.
USPC ..... Plt./384

(58) Field of Classification Search
USPC ..... Plt./384
See application file for complete search history.

(56) References Cited

PUBLICATIONS

Trademark record for 'Red Rocket', published Mar. 11, 2014, serial No. 86092234, Blanc Vineyards LLC, status: live.*
Trademark record for 'Red Rocket', published Sep. 22, 2009, serial No. 77737311, Tozer Seeds America LLC, status: live.*
Trademark record for 'Red Rocket', published Nov. 16, 1999, serial No. 75511715, Lacebark Inc., status: live.*

* cited by examiner

*Primary Examiner* — Anne Grunberg

(57) ABSTRACT

A new, distinct *Pennisetum alopecuroides* plant as shown and described, characterized by thick greyed-purple inflorescences on 75 cm stems that start in early September in northern Illinois.

1 Drawing Sheet

Latin name: *Pennisetum alopecuroides*.
Cultivar name: 'Red Rocket'.

BACKGROUND OF THE INVENTION

The present invention relates to a new form of *Pennisetum alopecuroides* plant named 'Red Rocket'. 'Red Rocket' is a seedling of an unnamed *Pennisetum alopecuroides,* not patented, characterized by thick greyed-purple inflorescences on 75 cm stems that start in early September in northern Illinois. The new plant is the result of a breeding program taking place at a wholesale perennial nursery since 2001. The seedling was grown by the inventor at a wholesale perennial nursery in Hebron, Ill. in 2010. The selection of the new plant was due to its thick greyed-purple inflorescences on 75 cm stems that start in early September in northern Illinois. Asexual, vegetative division propagation has been the only means of reproduction. Propagation has taken place at a wholesale perennial nursery Hebron, Ill. in 2011. To date these plants have remained uniform in height. The new *Pennisetum* has shown to be stable and identical in reproduction to the parent after making over 550 vegetative divisions from 2011 to 2013.

SUMMARY OF THE INVENTION

In the following description, color references are made to The Royal Horticultural Society Colour Chart. The new *Pennisetum alopecuroides* plant named 'Red Rocket' has shown the characteristic of thick greyed-purple inflorescences on 75 cm stems that start in early September in northern Illinois.

The parent plants were not available for comparison. Plants of the new *Pennisetum* can be compared to plants of *Pennisetum alopecuroides* 'Red Head', not patented. 1. The new *Pennisetum* has a height of 75 cm compared to the height of *Pennisetum alopecuroides* 'Red Head' which has a height of 120 cm. 2. The new *Pennisetum* has an inflorescence length of 15 cm compared to *Pennisetum alopecuroides* 'Red Head' which has an inflorescence length of 20 cm.

Plants of the new *Pennisetum* can be compared to plants of *Pennisetum alopecuroides* 'Hameln' not patented. 1. The new *Pennisetum* has a height of 75 cm compared to the height of *Pennisetum alopecuroides* 'Hameln' which has a height of 90 cm. 2. The new *Pennisetum* has an inflorescence length of 15 cm compared to *Pennisetum alopecuroides* 'Hameln' which has an inflorescence length of 10 cm. 3. The new *Pennisetum* has a greyed-purple inflorescence color compared to *Pennisetum alopecuroides* 'Hameln' which has a tan inflorescence color.

Plants of the new *Pennisetum* can be compared to plants of *Pennisetum alopecuroides* 'Mondry', not patented. 1. The new *Pennisetum* has a height of 75 cm compared to the height of *Pennisetum alopecuroides* 'Mondry' which has a height closer to 60 cm. 2. The new *Pennisetum* has an early September bloom time compared to *Pennisetum alopecuroides* 'Moudry' which typically blooms in October.

DESCRIPTION OF PHOTOGRAPHS

Figure 1:
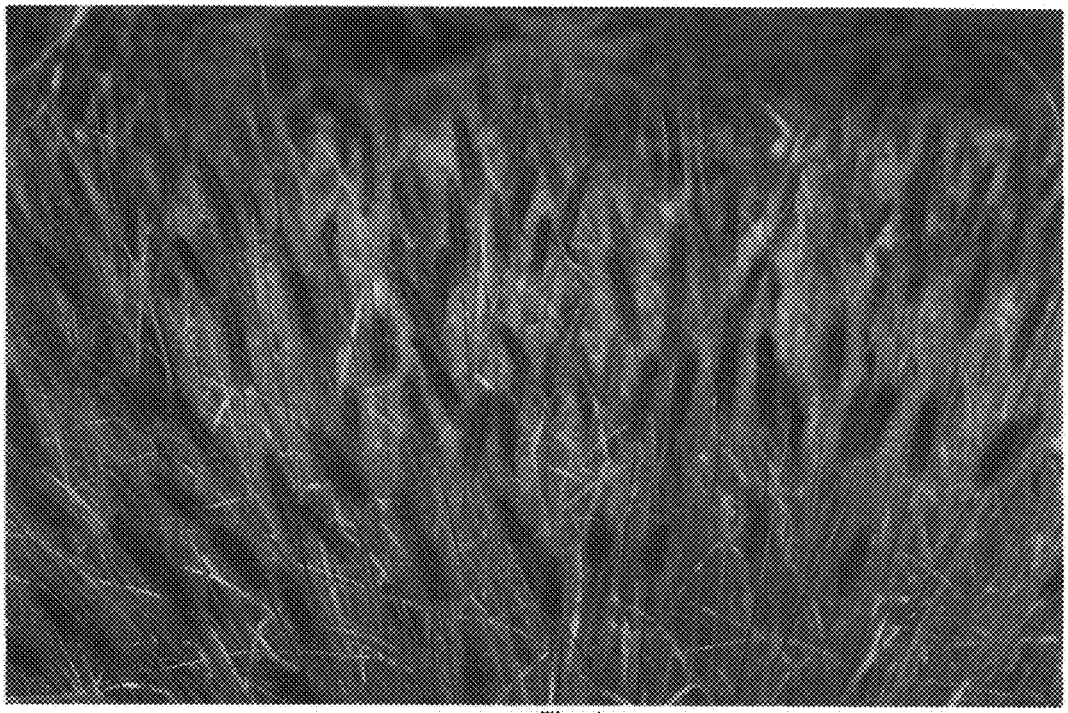

FIG. 1. Shows a group of potted 1 gallon plants in Hebron, Ill. USA.

Figure 2:
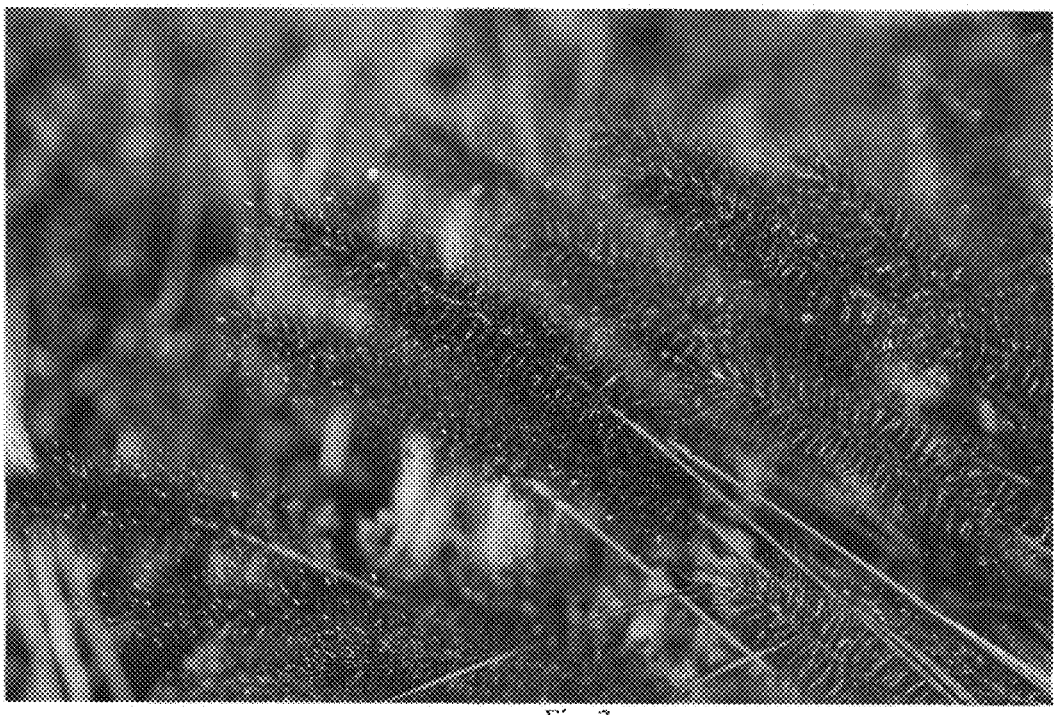

FIG. 2. Shows a close up of the flower in Hebron, Ill. USA.

DETAILED BOTANICAL DESCRIPTION

In the following description, color references are made to The Royal Horticultural Society Colour Chart (2001). The plant herein described is a one year old, three gallon specimen grown in full sun and irrigated in Hebron, Ill.

Botanical classification: *Pennisetum alopecuroides* cultivar 'Red Rocket'.

Parentage: *Pennisetum alopecuroides* unnamed seedling selections.

Propagation: Vegetative division.

Plant description: Overall habit of the new *Pennisetum* is strongly clumping mounds with uptight stems topped by greyed-purple colored inflorescences in early September. Vigor is moderate to fast.

*Plant height.*—75 cm.

*Plant width.*—50 cm.

*Stem diameter.*—6 mm.

*Stem color.*—146 C.

Foliage:

*Type*.—Deciduous, grass growing in culms.

*Shape*.—Blade.

*Petiole*.—None.

*Blade length.*—45 cm average, ranging from 16-59 cm.

*Width.*—8 mm.

*Adaxial leaf description*.—The leaf color is green color 137 B.

*Abaxial leaf description*.—The leaf color is green color 137 A.

*Basal leaf sheath color*.—Close to 137 A.

*Leaf sheath*.—Glabrous.

*Auricles*.—Not present.

*Ligules*.—As wide as the leaf blade, 1 mm tall, color close to 137 A.

*Collars*.—Continuous, as wide as the leaf blade, less than 1 mm tall, color close to 137 A. Leafbuds are folded in the bud stage.

*Rhizomes or stolons*.—None. The attitude of the tiller on the culm is erect, 35 degrees from the culm. The culm node is glabrous and color at the node is close to 137 A.

*Internode*.—Length 15-20 cm.

*Culm diameter and color at the internode.*—5-6 mm, close to 137 A.

*Fall leaf color*.—Mostly green 137 A with some N77 A fall color at the tips.

Flower inflorescence:

*Number of spike bearing tillers in the culmus.*—35.

*Inflorescence type*.—Terminal bristled spike.

*Floret color.*—145 A.

*Individual floret size.*—2 mm across, 7 mm tall.

*Anther coloration and size.*—183 C, 5 mm long, 0.5-1 mm wide.

*Stigma color and size*.—Close to 155 C, 11 mm long, 0.5 mm wide.

*Glume color and size*.—Close to 186 A, 2 mm, less than 1 mm wide.

*Bristle size.*—22 mm long, less than 1 mm wide.

*Bristle color.*—186 A.

*Caryopsis color.*—145 A, shape — elliptic.

*Overall inflorescence spike size.*—6 cm wide, 14 cm long.

*Flower number*.—Approximately 205 florets per mature spike measuring 6 cm wide, 15 cm long.

*Fertility*.—Self-fertile, Fertile with 3 Anthers and 3 Stamens, 1 Stigma.

*Blooming habit*.—Terminal bristled spike on up to 75 cm stems.

*Bloom period and duration*.—Mid-August into October.

*Scent*.—No scent noticed.

*Bloom color overall.*—186 A.

*Roots*.—Stiff, fibrous, and freely branching.

*Fruit*.—Seed identical to the species except size is a slightly smaller.

Disease resistance: Plants are not susceptible to any major pests or diseases.

I claim:

1. A new, distinct *Pennisetum alopecuroides* plant as shown and described, characterized by thick greyed-purple inflorescences on 75 cm stems that start in early September in northern Illinois.

* * * * *